(12) United States Patent
Marshall et al.

(10) Patent No.: US 8,449,498 B2
(45) Date of Patent: *May 28, 2013

(54) RELATING TO INJECTION DEVICES

(75) Inventors: Jeremy Marshall, Oxford (GB); Nick Hansen, Oxford (GB)

(73) Assignee: Owen Mumford Limited, Oxford (GB)

( * ) Notice: Subject to any disclaimer, the term of this patent is extended or adjusted under 35 U.S.C. 154(b) by 0 days.

This patent is subject to a terminal disclaimer.

(21) Appl. No.: 12/688,060

(22) Filed: Jan. 15, 2010

(65) Prior Publication Data

US 2010/0121272 A1    May 13, 2010

Related U.S. Application Data

(63) Continuation of application No. 10/485,087, filed as application No. PCT/GB02/03428 on Jul. 26, 2002, now Pat. No. 7,695,453.

(30) Foreign Application Priority Data

Jul. 28, 2001    (GB) .................................. 0118419.1

(51) Int. Cl.
*A61M 5/00*    (2006.01)
*A61M 5/32*    (2006.01)

(52) U.S. Cl.
CPC ............ *A61M 5/322* (2013.01); *A61M 5/3271* (2013.01)
USPC ......................................... 604/110; 604/198

(58) Field of Classification Search
USPC .................. 604/192–198, 110, 181, 187, 263, 604/224, 131–135, 208–210; 128/919
See application file for complete search history.

(56) References Cited

U.S. PATENT DOCUMENTS

| | | | |
|---|---|---|---|
| 3,882,863 A | 5/1975 | Sarnoff et al. | |
| 4,031,893 A | 6/1977 | Kaplan et al. | |
| 4,529,403 A * | 7/1985 | Kamstra | 604/136 |
| 5,026,349 A | 6/1991 | Schmitz et al. | |
| 5,405,362 A | 4/1995 | Kramer et al. | |
| 5,478,316 A | 12/1995 | Bitdinger et al. | |
| 5,599,309 A | 2/1997 | Marshall et al. | |
| 5,776,107 A | 7/1998 | Cherif-Cheikh | |
| 5,957,897 A | 9/1999 | Jeffrey | |
| 6,099,503 A * | 8/2000 | Stradella | 604/135 |
| 6,258,068 B1 | 7/2001 | Kirchhofer et al. | |
| 6,280,421 B1 | 8/2001 | Kirchhofer et al. | |
| 6,544,234 B1 * | 4/2003 | Gabriel | 604/207 |
| 6,626,863 B1 * | 9/2003 | Berler | 604/110 |
| 6,918,889 B1 | 7/2005 | Brunel | |
| 7,104,969 B2 | 9/2006 | Du Plessis | |

FOREIGN PATENT DOCUMENTS

| | | |
|---|---|---|
| DE | 198 21 933 | 11/1999 |
| EP | 0 956 873 | 11/1999 |
| FR | 2 794 650 | 12/2000 |

(Continued)

*Primary Examiner* — Matthew F DeSanto
(74) *Attorney, Agent, or Firm* — Young & Thompson

(57) ABSTRACT

An injection device for a syringe incorporates housing for a syringe. A needle shroud is captive to the leading end of the housing and is movable before use between extended and retracted positions. A drive member is releasable from a rearward position within the housing to urge the syringe forwards to project its needle beyond the retracted needle shroud and then to express a dose through the needle. Locating members on the housing capture the drive member at its forward position (attained after expressing the dose). The captured drive member is also arranged to block retraction of the needle shroud from its extended position.

19 Claims, 5 Drawing Sheets

FOREIGN PATENT DOCUMENTS

| | | |
|---|---|---|
| WO | 91 11212 | 8/1991 |
| WO | 97/14455 | 4/1997 |
| WO | 99/37343 | 7/1999 |
| WO | 02/47746 | 6/2002 |

* cited by examiner

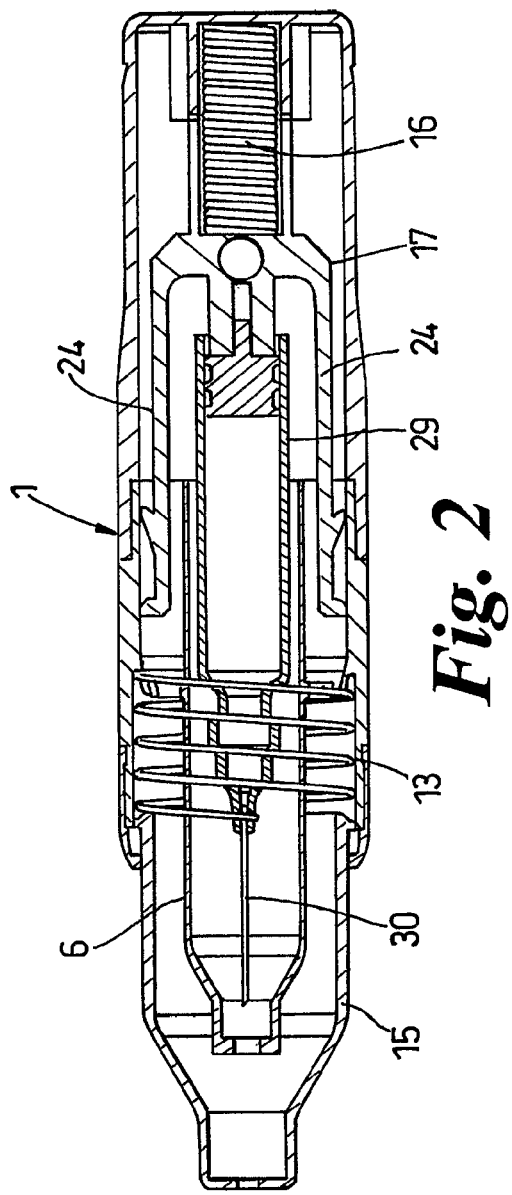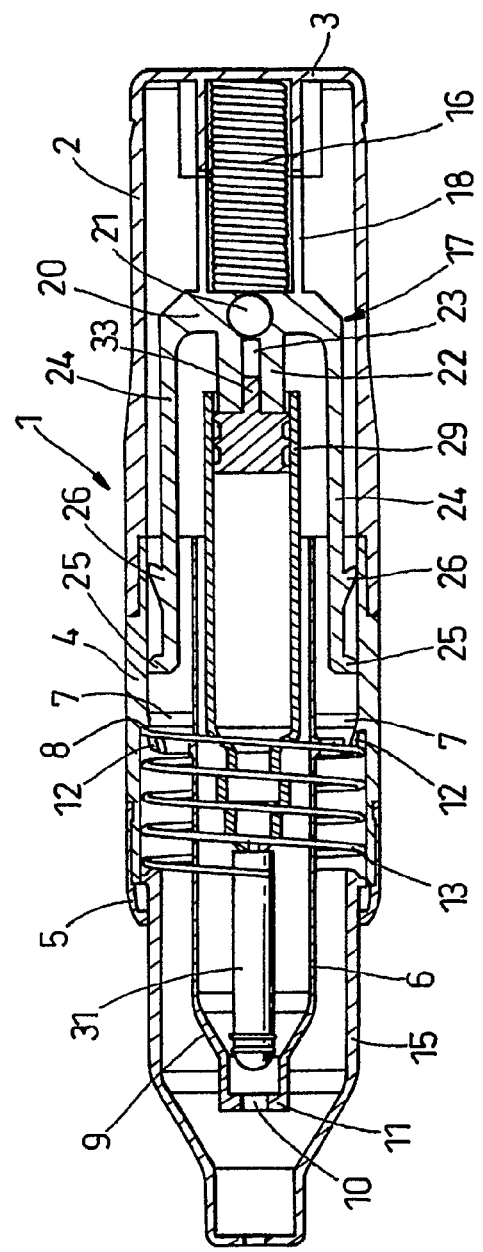

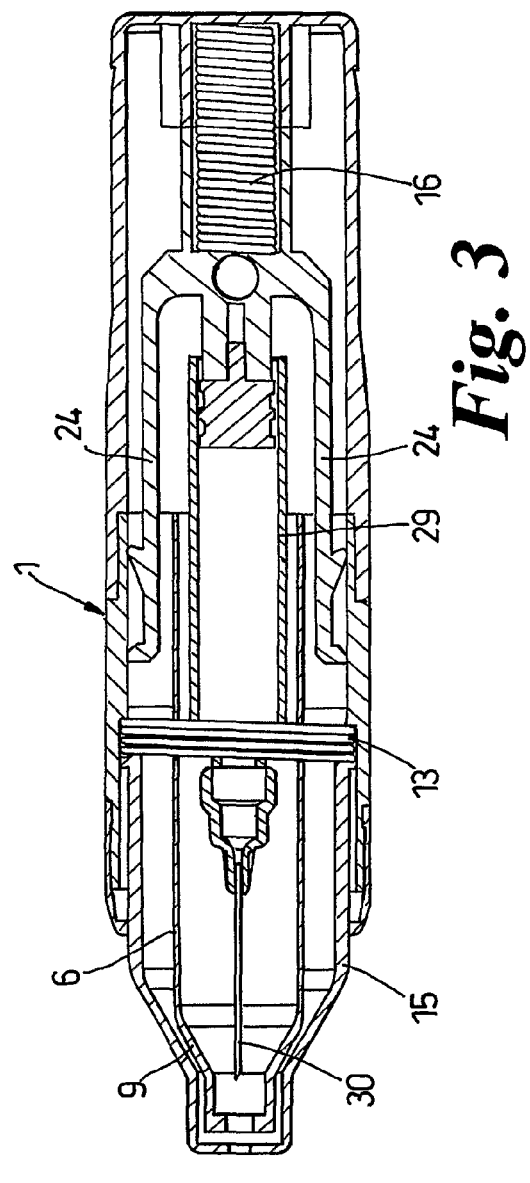
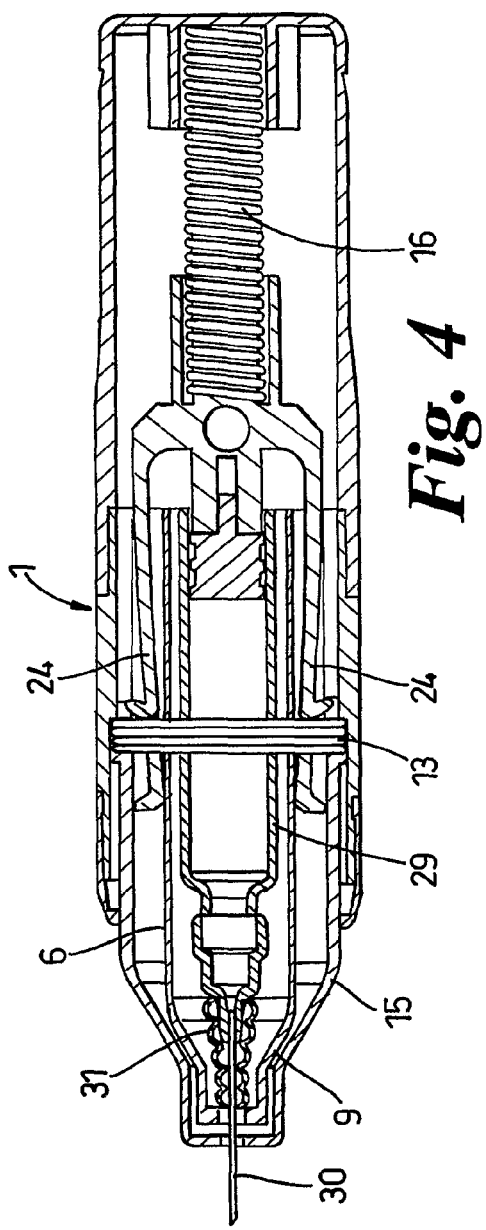

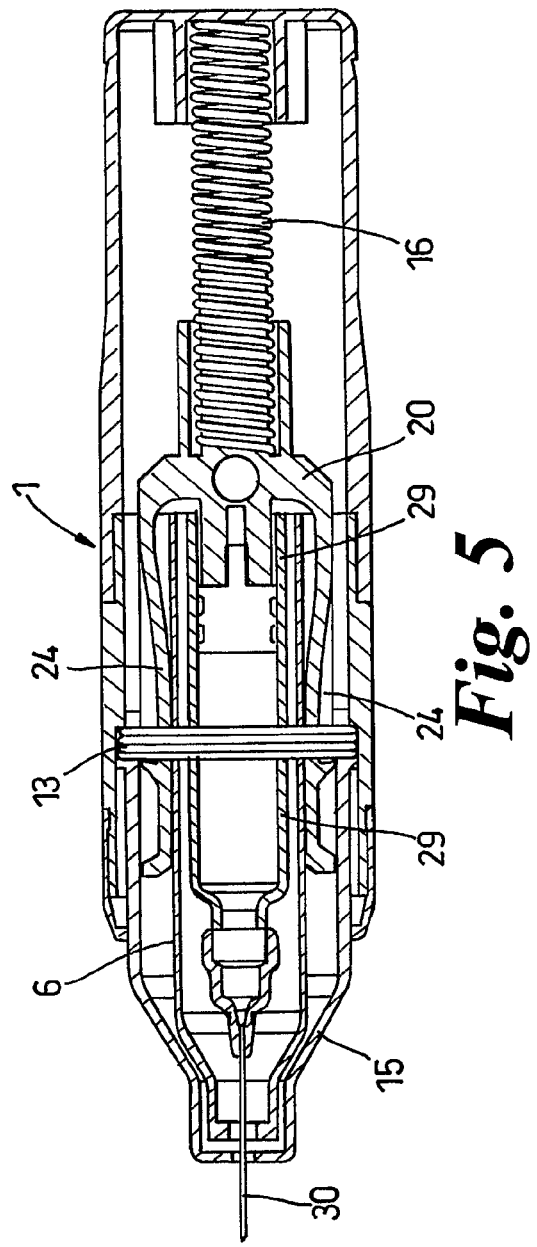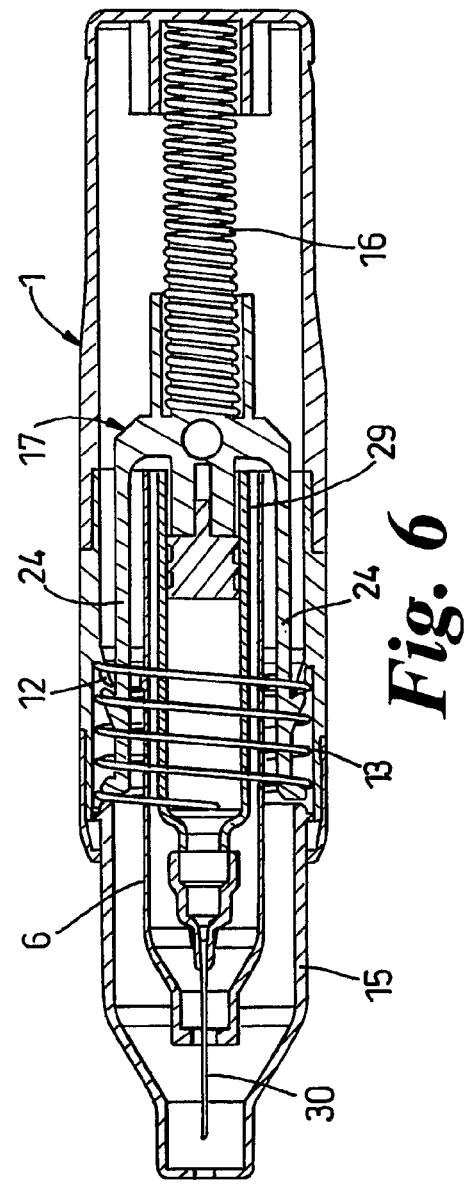

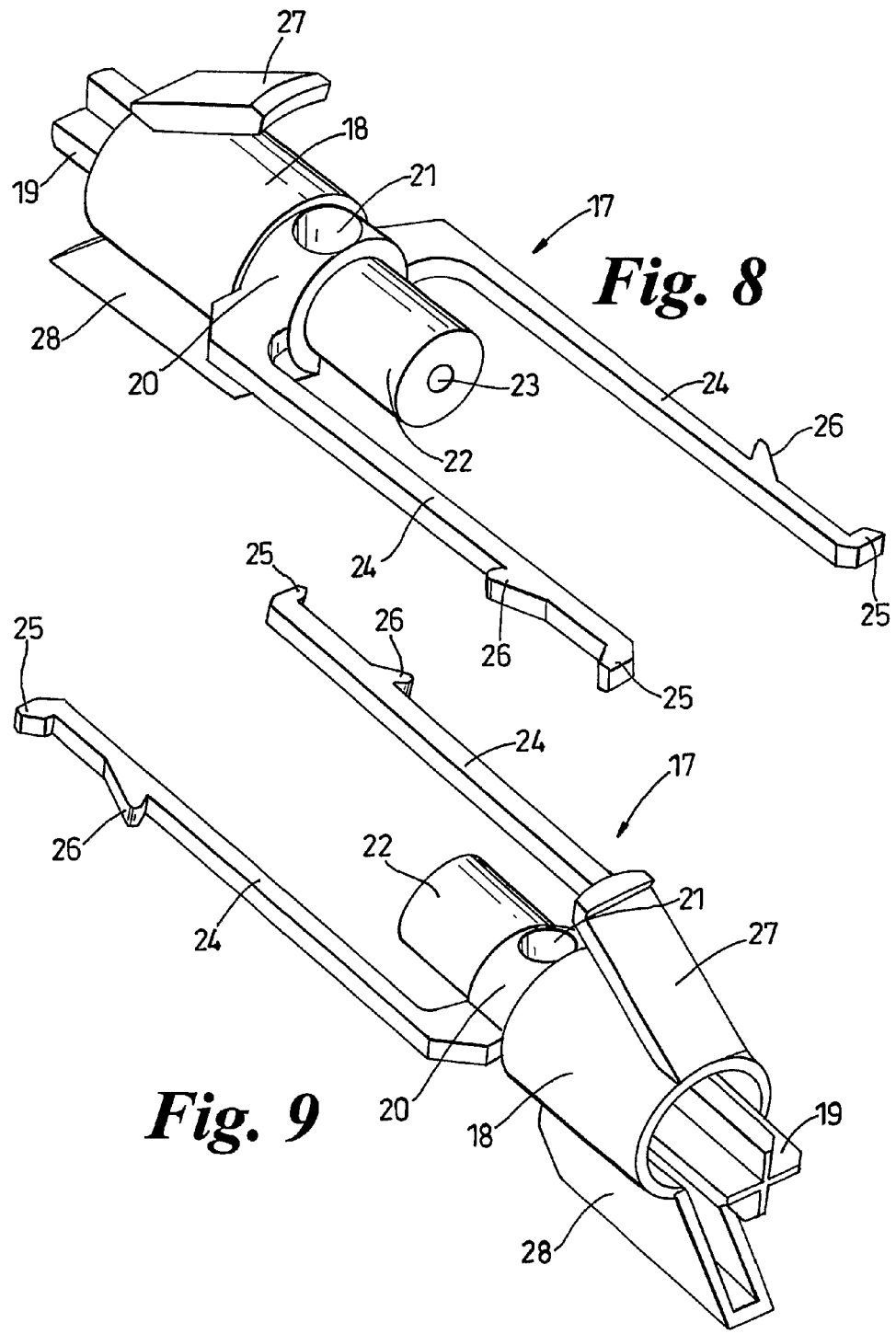

RELATING TO INJECTION DEVICES

CROSS REFERENCE TO RELATED APPLICATIONS

This application is a continuation of co-pending application Ser. No. 10/485,087 filed on Jun. 7, 2004, which is the 35 U.S.C. §371 national stage of International PCT/GB02/03428 filed on Jul. 26, 2002, which claims priority to British Application No. 0118419.1 filed on Jul. 28, 2001. The entire contents of each of the above-identified applications are hereby incorporated by reference. Any disclaimer that may have occurred during prosecution of the above referenced applications is hereby expressly disclaimed.

BACKGROUND OF THE INVENTION

This invention relates to injection devices. It is concerned with those where a syringe is enclosed in a housing of barrel-like form, the syringe being propelled forward by a drive mechanism to project its needle, followed by continued operation of the drive mechanism to push the plunger of the syringe and eject a dose. This will leave the needle sticking out, unless certain measures are taken. One answer is to have an arrangement for withdrawing the syringe back into the housing, while another is to have a needle shroud that moves out from the housing to enclose the needle. Of course, this must not interfere with the actual injection operation. It has therefore been proposed that the shroud is normally spring-urged forwardly to a needle protecting position, but when the device is pushed against the patient's skin the shroud is forced to retract against its spring. After injection, the spring pushes the shroud forwards again.

It is desirable for there to be an arrangement for automatically locking the shroud at its fully projecting position after the injection but not before, and it is the aim of this invention to provide a way of achieving this.

SUMMARY OF THE INVENTION

According to the present invention there is provided an injection device for a syringe, the device comprising a housing for the syringe, a needle shroud captive to the leading end of the housing and movable before use between extended and retracted positions, a drive member releasable from a rearward position within the housing to urge the syringe forwards to project its needle beyond the retracted needle shroud and then to express a dose through the needle, and locating members on the housing for capturing the drive member at its forward position attained after expressing the dose, and wherein the captured drive member is arranged to block retraction of the needle shroud from its extended position.

The needle shroud will normally be biased forwardly so that, in use, as the device is pressed against the skin, the shroud is pushed back into the housing. The user will then release the drive member.

That drive member will generally be spring-actuated, and in the preferred form it will have a plunger that enters the rear end of the syringe to engage the piston within the syringe, thereby supporting the syringe at its rear end. The needle of the syringe will ideally have a collapsible rubber sheath, which acts as a support for the forward end of the syringe. The tip of the sheath may be located in a small cup-like formation of the housing with a central aperture through which the needle, but not the sheath, can penetrate. As the syringe is driven forwards, the needle pierces the sheath to project through and beyond the cup-like formation while the sheath "concertinas" into a shorter length, helping to arrest the syringe when it is fully compressed.

The drive member may have arms that extend forwardly to co-operate with the interior of the housing and the needle shroud. As the drive member moves forwards, these arms can be flexed inwards by locating formations on the housing to cause their leading ends to enter the retracted needle shroud. After the injection, as the needle shroud is released and moves forwards, it passes beyond the arms, which disengage and flex back outwards. Abutments on the outsides of the arms can then be provided to be in registry with abutments on the inside of the housing, after completion of the injection operation, so that the drive member cannot be pushed back. Preferably these abutments will be hooked for positive interengagement. At the same time, after completion of the injection operation, the ends of the arms are ideally aligned with the needle shroud, and provide abutments to prevent the shroud being pushed back.

BRIEF DESCRIPTION OF THE DRAWINGS

For a better understanding of the invention, one embodiment will now be described, by way of example, with reference to the accompanying drawings, in which:

FIGS. 1 to 6 are axial sections of an injection device in various stages from pre-use to post-use.

DETAILED DESCRIPTION OF THE PREFERRED EMBODIMENTS

Figure 7:
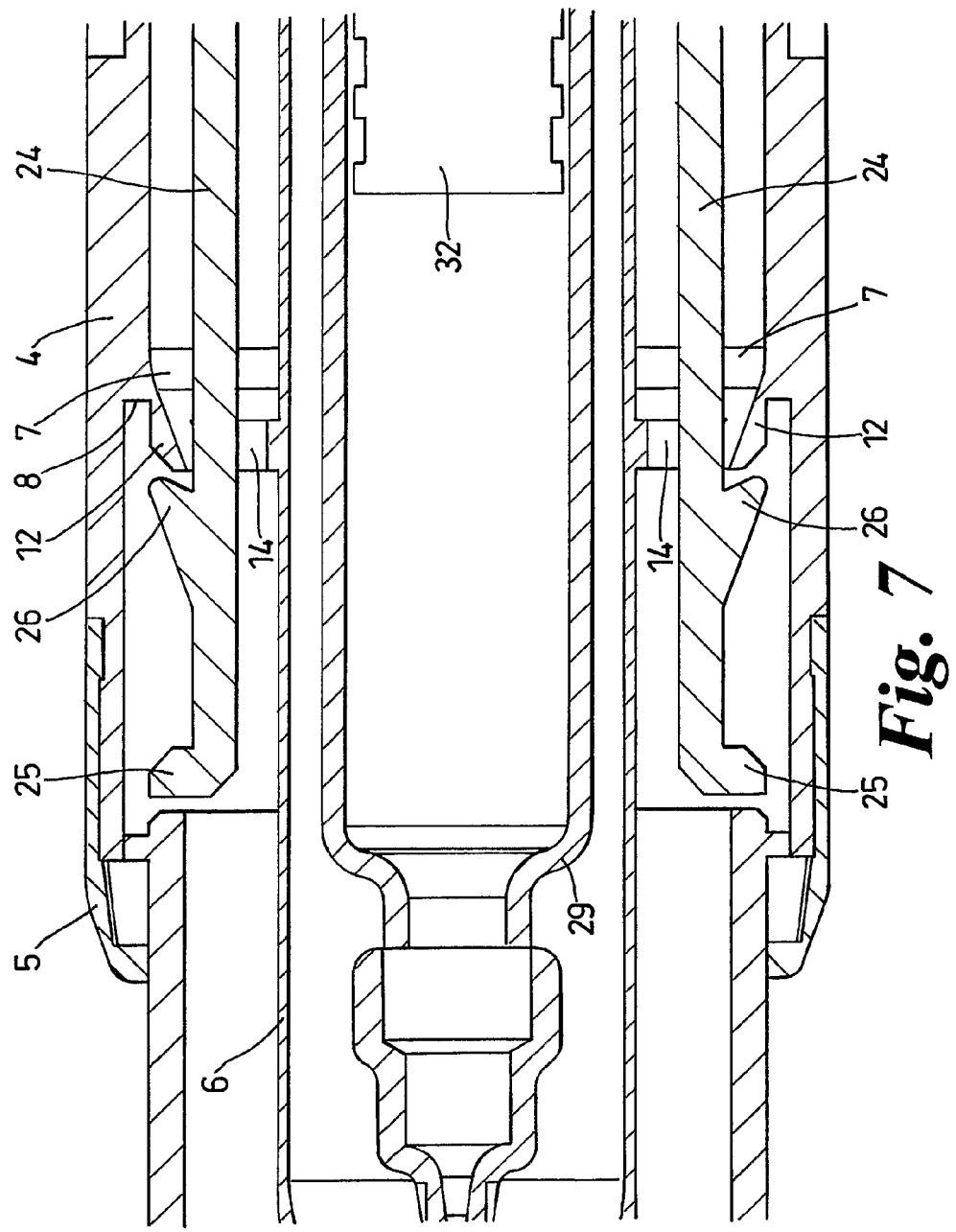
FIG. 7 is an enlarged detail of FIG. 6, and FIGS. 8 and 9 are perspective views of a drive member of the device.

The injection device has a composite barrel 1 with a rear portion 2 having a closed rear end 3, an intermediate portion 4, and a forward portion 5. The intermediate portion 4 carries a co-axial inner tube 6 by radial spokes 7 immediately to the rear of a forward facing inner shoulder 8. The leading end 9 of the tube 6 constricts and has a small aperture 10 formed by an inward annular flange 11 at its extremity. Two diametrically opposed lugs project inwardly and forwardly from the shoulder 8, which locates the rear end of a helical spring 13. Cradle-like or U-shaped guides 14 as best seen in FIG. 7 are formed on the outside of the tube 6 directly opposite these lugs 12. At its forward end the spring 13 bears against a needle shroud 15 made captive to the barrel by the forward portion 5 but capable of sliding backwards, telescoping further into the barrel to compress the spring 13 and to nest closely over the leading end 9 of the tube 6.

The rear end 3 internally provides a seat for a drive spring 16 which acts on a drive member 17 as best seen in FIGS. 8 and 9. It has a hollow cylindrical portion 18 to receive the forward end of the spring 16, which also locates around an x-section stem 19 co-axially within the portion 18 and projecting rearwardly beyond it. Forward of this, the cylinder 18 steps inwards to a co-axial intermediate portion 20 solid apart from a transverse bore 21, and then steps further inwards into a co-axial plunger with a central bore 23 open to its leading end. Branching out and then forwardly from the intermediate portion 20 there are two diametrically opposed arms 24 with outwardly projecting lugs 25 at their free ends, and each with a tooth 26 a short distance back from the lug 25. Each tooth 26 slopes at an acute angle outwardly and rearwardly and then slants back in at a less acute angle. On one side the cylinder 18 has a forwardly and outwardly projecting tongue 27 which is part of the trigger mechanism for releasing the drive member 17, and opposite that tongue there is a longitudinal heel 28 which can run in a track (not shown) formed on the inside of the barrel 1 to ensure that the drive member 17 is correctly orientated and runs true.

A conventional syringe 29 is co-axially carried within the tube 6. Its needle 30 has a rubber sheath 31 whose closed forward end locates in the cup-like leading end 9 of the tube 6. The sheath 31 is never removed, but it is shown only in FIGS. 1 and 4. The plunger 22 of the drive member 17 enters the rear end of the syringe and co-operates with its piston 32, which has a rear central stud 33 that locates in the bore 23. The syringe 29 is thus carried co-axially within the tube 6 by the tip of the sheath 31 and the stud 33: there is no contact between the body of the syringe and the tube 6.

Initially, the device is made safe by a pin (not shown) transversely through the barrel 1 and through the bore 21, locking the drive member 17 in its rearward position with the spring 16 compressed, as in FIG. 1. When this pin is removed, the device can be fired. The user first presses the leading end of the needle shroud 15 against the area to be injected and urges the device forwards. The needle shroud 15 is forced back until the spring 13 is fully compressed. The sheathed tip of the needle 30 is still within the device, which has now reached the position of FIG. 3.

The trigger is operated, allowing the spring 16 to act, and that drives the member 17 forwards. The effective solidity of the dose within the syringe 29 causes that to be moved forwards to project the needle 30, which pierces the end of the sheath 31, leaving that to concertina into a short length within the leading end 9 as indicated in FIG. 4. It is too bulky to pass through the aperture 10. The needle 30 therefore enters the flesh. During this movement, the lugs 25 and 12 meet. The latter may be deflected slightly outwardly but any such movement will be limited by the compressed spring 13. The arms 24, however, will be flexed inwardly, allowing the lugs 25 to snap past and bear outwardly against the inside of the shroud 15. The arms 24 start to pass through the guides 14 at this time and they help to keep the arms properly aligned. The syringe 29 reaches the limit of its forward movement by the sheath 31 becoming fully compressed, the teeth 26 simultaneously coming up against the rear sloping sides of the lugs 12. This is the position of FIG. 4.

Continued forward movement of the member 17 ejects the dose through the needle 30 and causes the teeth 26 and lugs 12 to act as wedges and flex the arms 24 further inwards. The teeth 26 go past the lugs 12 just before the injection is finished, which is when the intermediate portion 20 of the drive member 17 comes up against the rear end of the syringe, as shown in FIG. 5. The device is then withdrawn, and this allows the spring 13 to act and push the needle shroud 15 forward again, sliding free of the teeth 26 and then the lugs 25. The arms 24 can then spring outwards again to their natural positions, and this causes the teeth 26 to hook with the lugs 12 if there is any reverse movement. If the needle shroud 15 is pushed back against the lugs 25 and then twisted, pushing the ends of the arms 24 circumferentially, the guides 14 will resist this and keep the teeth 26 in registry with the lugs 12.

Thus, the drive member 17 is held against retraction, while the needle shroud 15, still trapped by the forward barrel portion 5 against removal, is prevented from rearward movement by abutment with the lugs 25. The needle 30, therefore, although still projecting from the tube 6, is safely inside the shroud 15.

What is claimed is:

1. An injection device for a syringe having a needle, the device comprising:
    a housing for receiving in use a syringe for movement with respect thereto;
    a needle shroud captive to a leading end of the housing and movable before use between extended and retracted positions;
    a drive member configured to move from a rearward position within the housing to urge the syringe and thereby move the syringe forward in the housing to project the needle beyond the needle shroud when the needle shroud is in the retracted position, and then to a forward position to express a dose through the needle; and
    locating members on a sidewall of the housing, said locating members configured to, upon arrival of the drive member into the forward position, capture and maintain the drive member at the forward position attained after expressing the dose, the captured drive member being prevented by said locating members from rearwardly exiting the forward position,
    wherein, when the drive member is captured by the locating members, a blocking portion of the drive member is positioned to stop a rearward retraction of the needle shroud from the extended position and, with the drive member captured by the locating members and stopping the needle shroud from retracting from the extended position, an entire length of the needle is shrouded by said needle shroud.

2. The injection device according to claim 1, wherein the drive member has arms that extend forwardly to co-operate with an interior of the housing and the needle shroud.

3. The injection device according to claim 2, wherein locating formations on the housing are provided to cause leading ends of the arms to be flexed inwards and to enter the retracted needle shroud.

4. The injection device according to claim 3, wherein the arms include outward facing abutments that are in registry with said locating formations on the inside of the housing, so that when the dose has been expressed, the drive member is prevented from being pushed back from the forward position.

5. The injection device according to claim 4, wherein said abutments are hooked for positive interengagement.

6. The injection device according to claim 2, wherein the ends of the arms are aligned with the needle shroud when the injection operation is complete, and provide abutments to prevent the needle shroud from being pushed back from the extended position to the retracted position.

7. The injection device according to claim 1, wherein the drive member is spring-actuated.

8. The injection device according to claim 7, wherein the drive member has a plunger that enters a rear end of the syringe to engage a piston within the syringe, thereby supporting the syringe at the rear end.

9. The injection device according to claim 1, wherein the needle of the syringe has a collapsible rubber sheath which acts as a support for a forward end of the syringe.

10. The injection device according to claim 9, wherein a tip of the sheath is located in a small cup-like formation of the housing provided with a central aperture through which the needle, but not the sheath, can penetrate.

11. The injection device according to claim 1, wherein the needle shroud is biased forwardly so that, in use, when the device is pressed against the skin, the shroud is pushed back into the housing.

12. The injection device according to claim 1, wherein the drive member is provided with respective abutment surfaces that snap past the locating members on the side wall of the housing as the drive member moves towards said forward position, the locating members configured to cooperate with the abutment surfaces to capture said drive member and prevent said drive member from returning from the forward position.

13. The injection device according to claim 1, wherein the locating members and the drive member are configured to enter into locking engagement with each other upon arrival of the drive member into the forward position, the locking engagement preventing the drive member from exiting the forward position by a rearward movement.

14. The injection device according to claim 1, wherein the drive member comprises elements configured to pass over the locating members during a forward movement of the drive member from the rearward position to the forward position and, upon passing the locating members, engage in locking engagement with the locating members to stop a rearward movement of the drive member from the forward position.

15. An injection device for a syringe having a needle, the device comprising:
- a housing for receiving in use a syringe movable with respect thereto;
- a needle shroud captive to a leading end of the housing and movable before use between extended and retracted positions;
- a drive member, movable within the housing from a rearward position to a terminal forward position to push the syringe forward in the housing such that the needle of the syringe projects outside the needle shroud when the needle shroud is in the retracted position and then to cause the syringe to express a dose through the needle before reaching the forward position; and
- locating members, on a sidewall of the housing, configured to engage in a locking engagement with portions of the drive member such that the locking members capture the drive member and stop the drive member from exiting the forward position attained by the drive member after expressing the dose, wherein, when the drive member is in locking engagement with the locating members, an abutment portion of the captured drive member obstructs a rearward motion of the needle shroud from the extended position thereby preventing the needle shroud from rearwardly exiting the extended position and, with the drive member captured by the locating members and obstructing the needle shroud from retracting from the extended position, an entire length of the needle is shrouded by said needle shroud.

16. The injection device according to claim 15, wherein the drive member has a plunger that enters a rear end of the syringe to engage a piston within the syringe, thereby supporting the syringe at the rear end.

17. The injection device according to claim 15, wherein the abutment portion of the drive member comprises an arm configured to co-operate with locating formations on an interior of the housing, the locating formations configured to cause an end of the arm to flex into a position for engagement with the needle shroud.

18. The injection device according to claim 15, wherein the abutment portion of the drive member comprises a flexible arm that, when the drive member is captured in the forward position, is in alignment with a portion of the needle shroud such that, upon application of a rearward force to the needle shroud, the abutment portion engages with the needle shroud and prevents the needle shroud from exiting the extended position.

19. The injection device according to claim 15, wherein the drive member comprises elements configured to pass over the locating members during a forward movement of the drive member from the rearward position to the forward position and, upon passing the locating members, engage in locking engagement with the locating members to stop a rearward movement of the drive member from the forward position.

* * * * *